United States Patent
Zheng et al.

(10) Patent No.: US 10,086,219 B2
(45) Date of Patent: Oct. 2, 2018

(54) AUTOMATIC SWITCHING DEVICE FOR A BREATHING APPARATUS WITH AN ALARM-RELIEF FUNCTION AND AUTOMATIC RESET

(71) Applicant: Honeywell International Inc., Morristown, NJ (US)

(72) Inventors: Jimmy Zheng, Shanghai (CN); Gilles Cordier, Terny Sorny (FR)

(73) Assignee: Honeywell International Inc., Morris Plains, NJ (US)

( * ) Notice: Subject to any disclaimer, the term of this patent is extended or adjusted under 35 U.S.C. 154(b) by 624 days.

(21) Appl. No.: 14/766,688

(22) PCT Filed: Jan. 23, 2014

(86) PCT No.: PCT/US2014/012684
§ 371 (c)(1),
(2) Date: Aug. 7, 2015

(87) PCT Pub. No.: WO2014/123695
PCT Pub. Date: Aug. 14, 2014

(65) Prior Publication Data
US 2015/0367150 A1 Dec. 24, 2015

Related U.S. Application Data

(60) Provisional application No. 61/762,729, filed on Feb. 8, 2013.

(51) Int. Cl.
*A62B 9/02* (2006.01)
*A62B 7/02* (2006.01)
(Continued)

(52) U.S. Cl.
CPC .............. *A62B 9/02* (2013.01); *A62B 7/02* (2013.01); *A62B 9/006* (2013.01); *A61M 16/20* (2013.01); *Y10T 137/2569* (2015.04)

(58) Field of Classification Search
CPC .. A61B 9/00; A61B 9/006; A61B 9/02; A61B 9/022; A61B 7/00; A61B 7/02;
(Continued)

(56) References Cited

U.S. PATENT DOCUMENTS 3,785,333 A * 1/1974 Warncke .......... A61M 16/0051
116/70
3,910,222 A * 10/1975 Metivier .......... A61M 16/0051
116/70
(Continued)

FOREIGN PATENT DOCUMENTS

CN      1374136 A    10/2002
CN    200954322 Y    10/2007
(Continued)

OTHER PUBLICATIONS

PCT/US2014/012684, PCT International Search Report and Written Opinion, dated Jul. 29, 2014, 11 pages.
(Continued)

*Primary Examiner* — Jackie Tan-Uyen T Ho
*Assistant Examiner* — Joseph D Boecker
(74) *Attorney, Agent, or Firm* — Wick Phillips Gould & Martin LLP

(57) ABSTRACT

Apparatus and associated methods relate to an automatic fluid alarm that provides a fluid-communication path between a secondary fluid source and a whistle port when a primary fluid source experiences a reduction in pressure, the automatic fluid alarm being user resettable by disconnecting the primary fluid source or otherwise reducing the primary source pressure and activating a reset member, thereby interrupting the fluid-communication path. In some examples, a piston member may provide a movable seal for providing the fluid-communication path and its interruption. An exemplary piston member may be slidably reset in a
(Continued)

non-interrupting mode by an adequate primary fluid pressure, and slidably set in an interrupting mode by a user activation. The interrupting mode may silence the whistle which may facilitate user communication during what may be a stressful primary fluid source failure event. Some exemplary automatic fluid alarms may conserve secondary fluid when the whistle is silenced.

20 Claims, 19 Drawing Sheets

(51) Int. Cl.
    *A62B 9/00*            (2006.01)
    *A61M 16/20*         (2006.01)

(58) Field of Classification Search
    CPC . A61B 7/12; A61M 16/0051; A61M 16/0816; A61M 16/0883; A61M 16/0891; A61M 16/20; A61M 16/208; A61M 16/209; A61M 2205/581; B63C 11/22; B63C 11/24; Y10T 137/2567; Y10T 137/2569
    USPC .................................................. 137/112, 113
    See application file for complete search history.

(56) References Cited

U.S. PATENT DOCUMENTS

| | | | | |
|---|---|---|---|---|
| 4,173,986 A | * | 11/1979 | Martin | A62B 9/02 128/205.24 |
| 4,181,126 A | * | 1/1980 | Hendry | A62B 7/06 114/315 |
| 4,237,813 A | * | 12/1980 | Howison | A61M 16/0051 116/70 |
| 4,739,790 A | * | 4/1988 | Clarke | B63C 11/18 128/205.24 |
| 4,870,960 A | * | 10/1989 | Hradek | B01D 53/0446 128/202.22 |
| 5,127,426 A | * | 7/1992 | D'Archambaud | A62B 9/02 137/113 |
| 2009/0107560 A1 | * | 4/2009 | Johnston | G05D 16/0605 137/113 |
| 2011/0088794 A1 | * | 4/2011 | Cavagna | F23K 5/007 137/557 |

FOREIGN PATENT DOCUMENTS

| | | | |
|---|---|---|---|
| CN | 104968397 A | 10/2015 | |
| DE | 19934078 A1 | 2/2001 | |
| EP | 0202721 A1 * | 11/1986 | ............... A62B 9/02 |
| EP | 2953688 A2 | 12/2015 | |
| FR | 2692635 A1 | 12/1993 | |
| GB | 2058580 A | 4/1981 | |
| WO | 2014123695 A2 | 8/2014 | |

OTHER PUBLICATIONS

China Patent Application No. 201480008019.9, Search Report, dated Jul. 31, 2017, 2 pages.

China Patent Application No. 201480008019.9, First Office Action, dated Aug. 3, 2017, 4 pages.

PCT/US2014/012684, PCT International Preliminary Report on Patentability, dated Aug. 11, 2015, 8 pages.

* cited by examiner

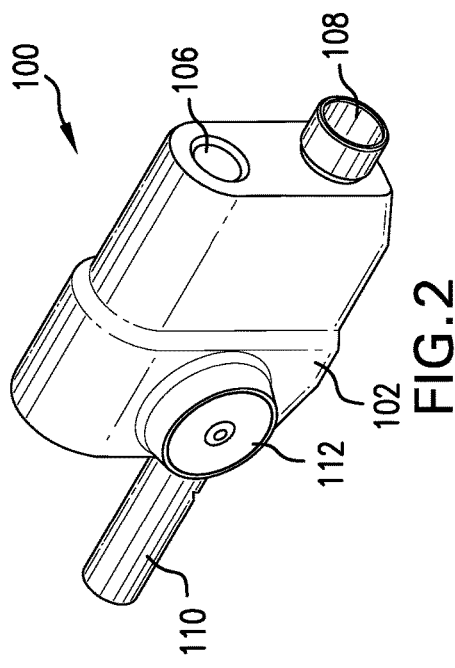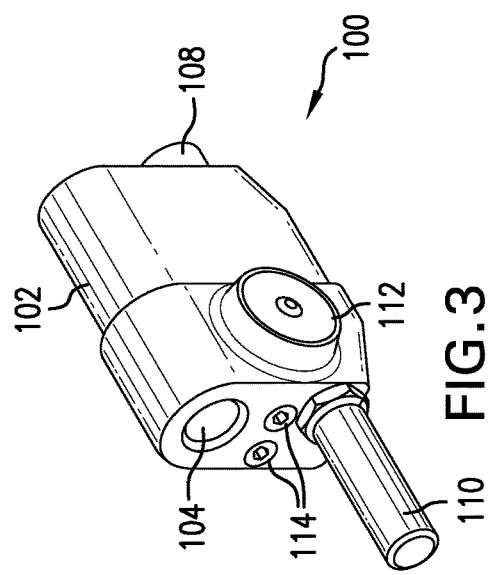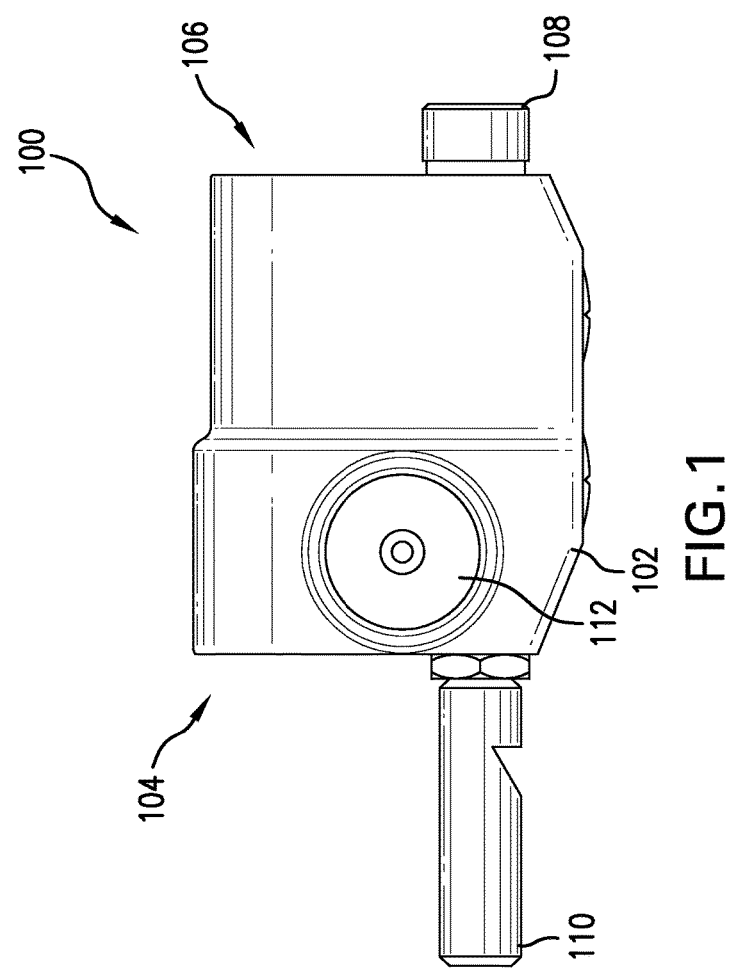

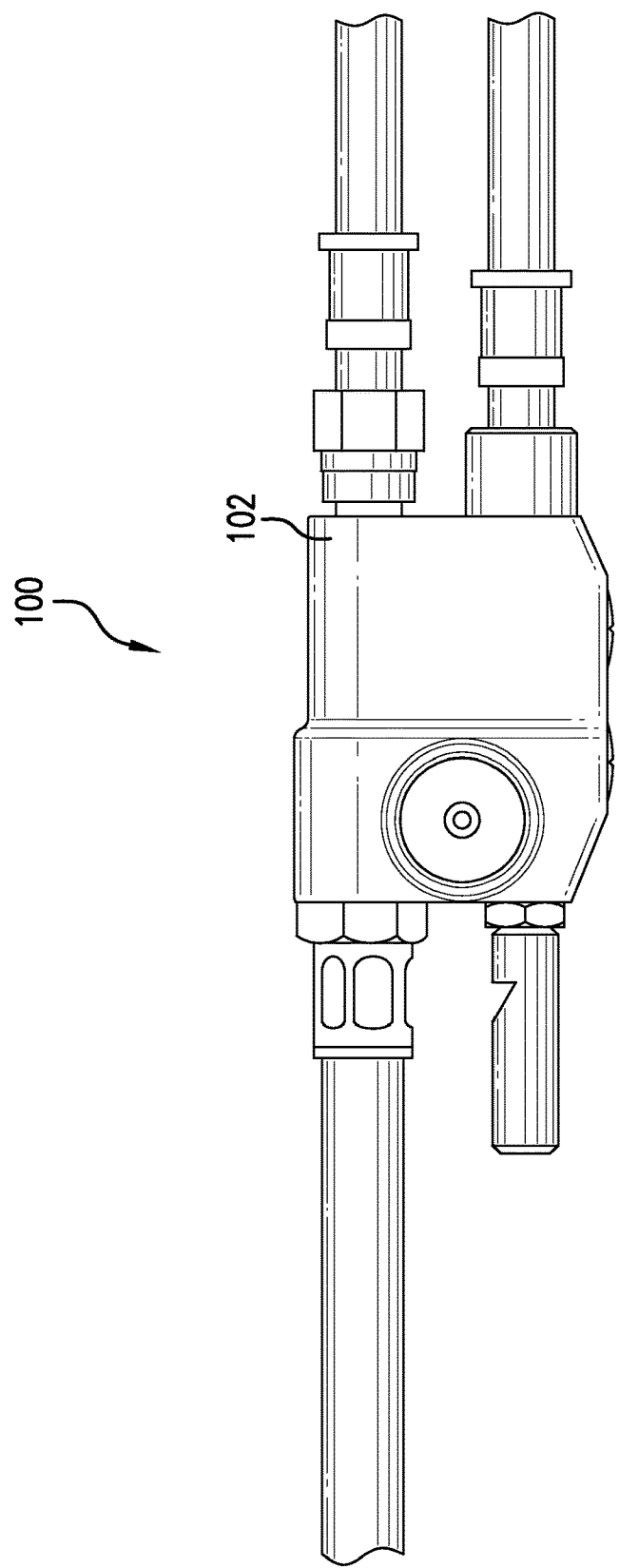

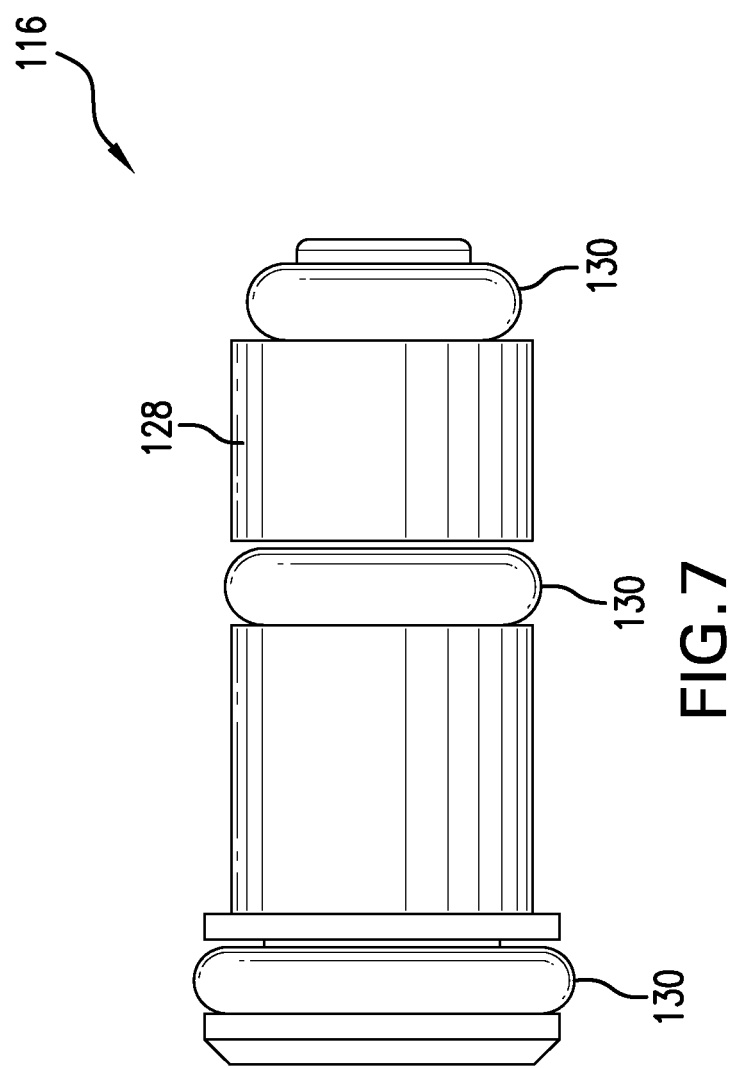

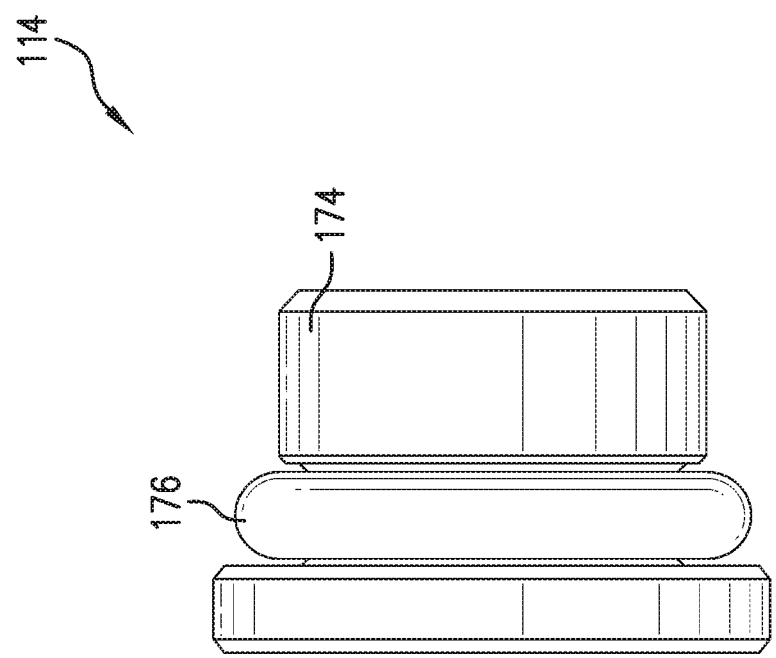

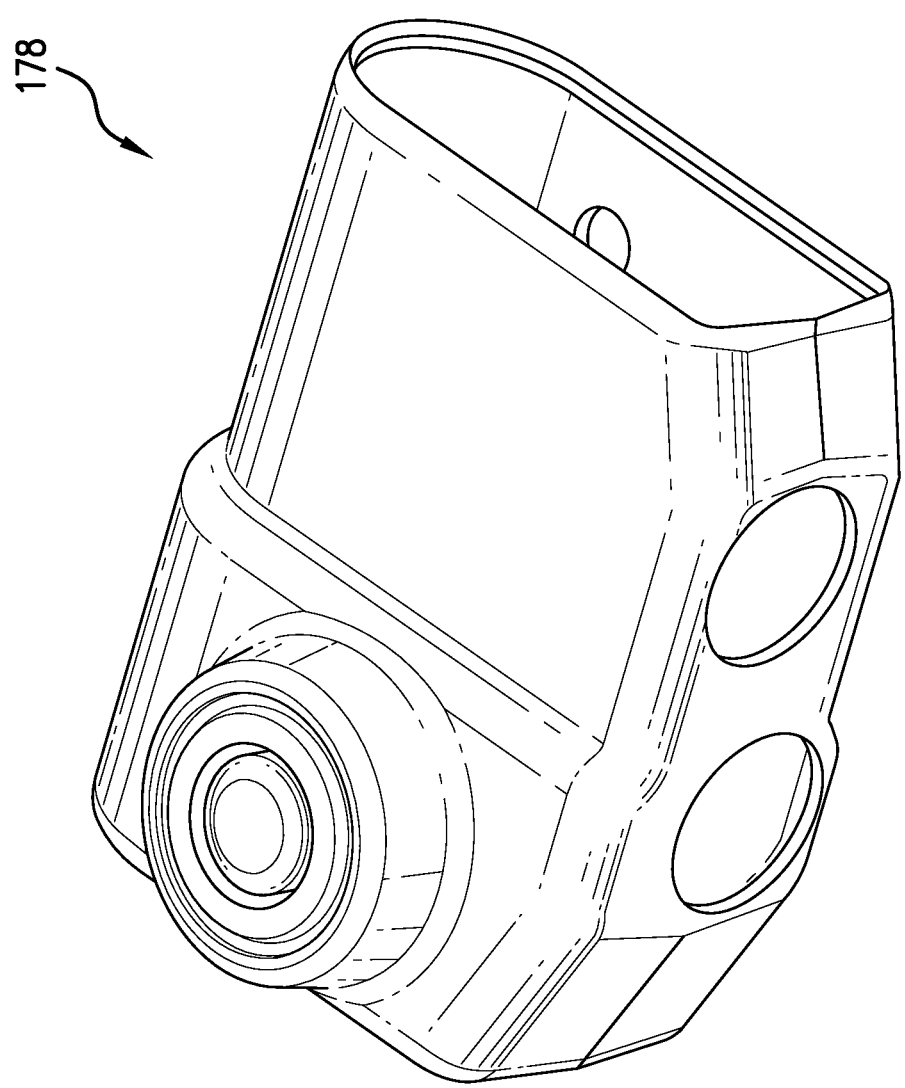

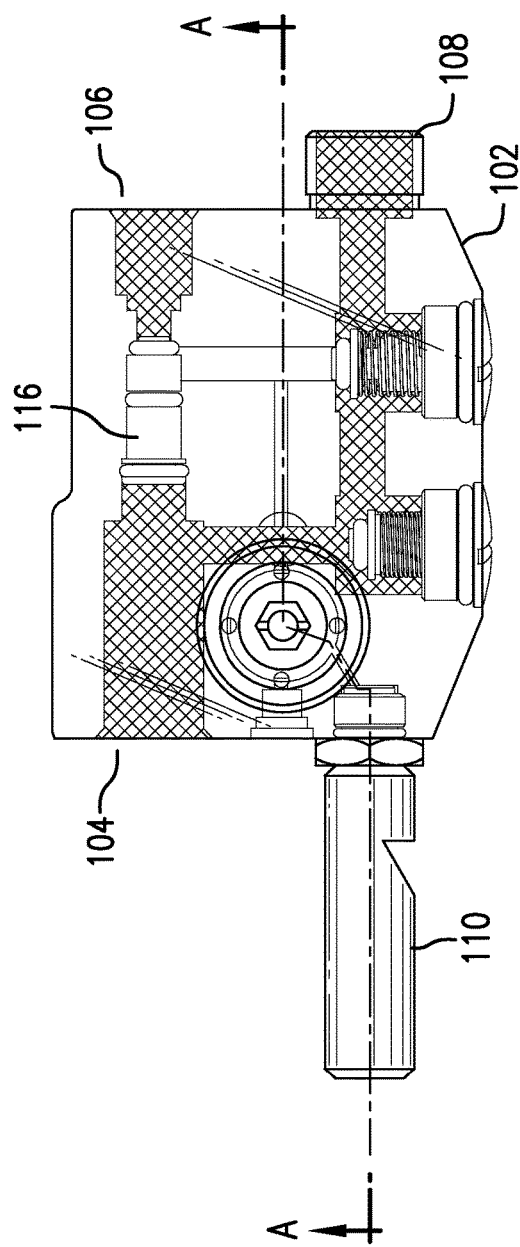
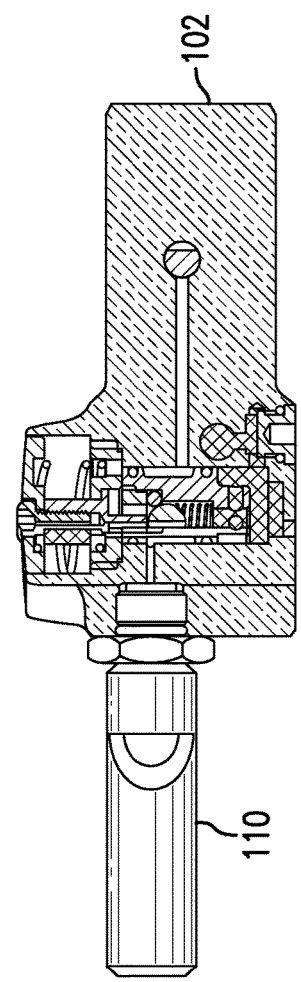
FIG. 14A
FIG. 14B

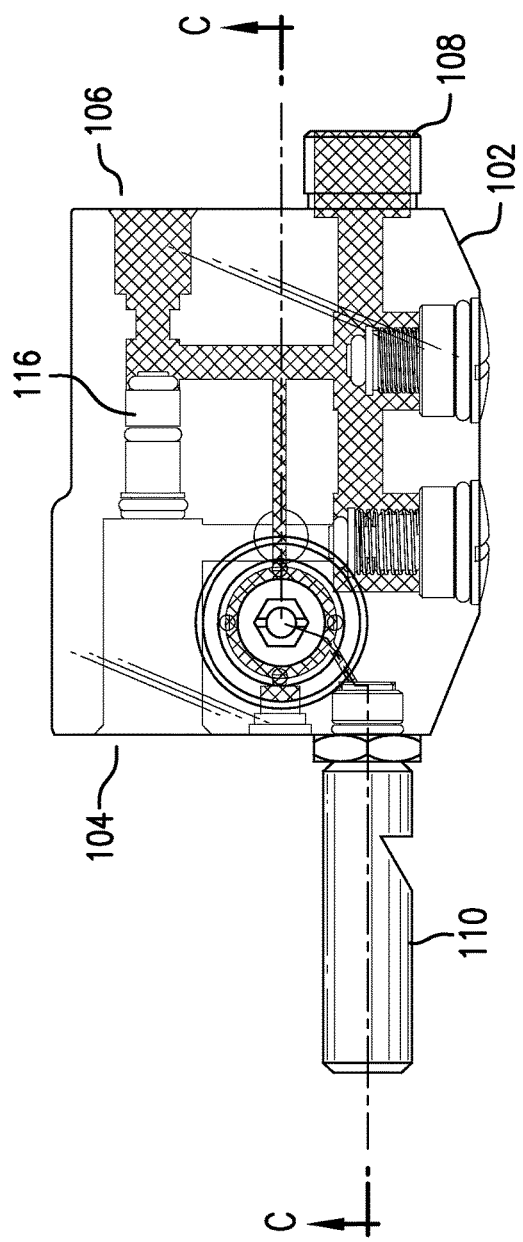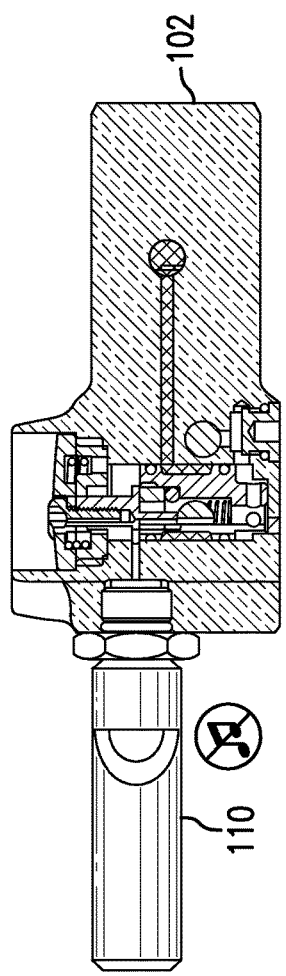
FIG.16A
FIG.16B

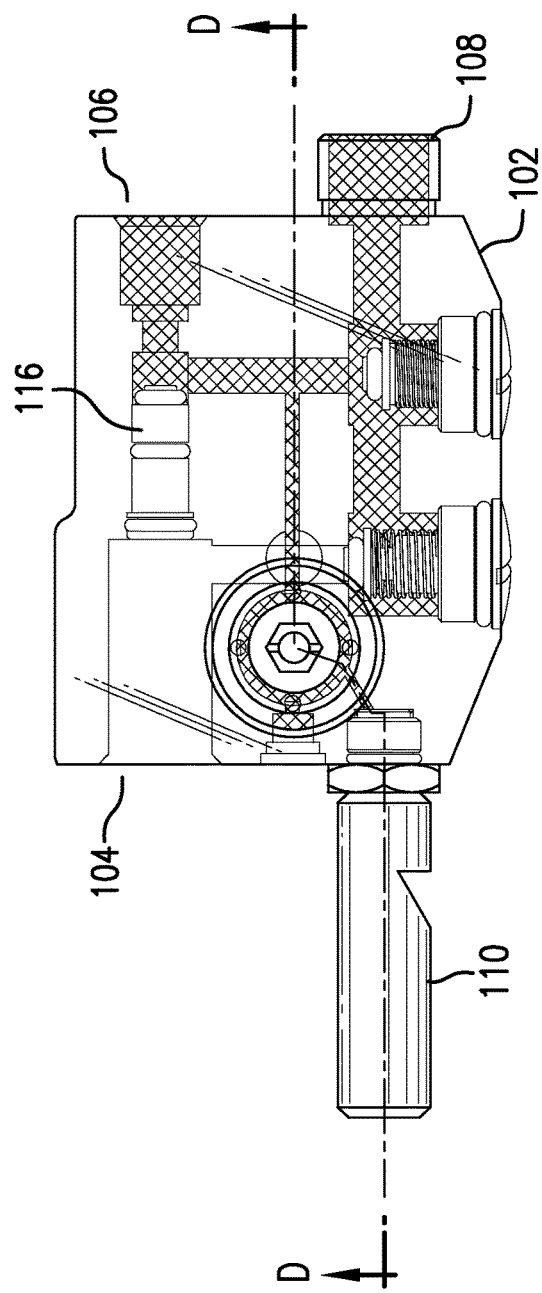
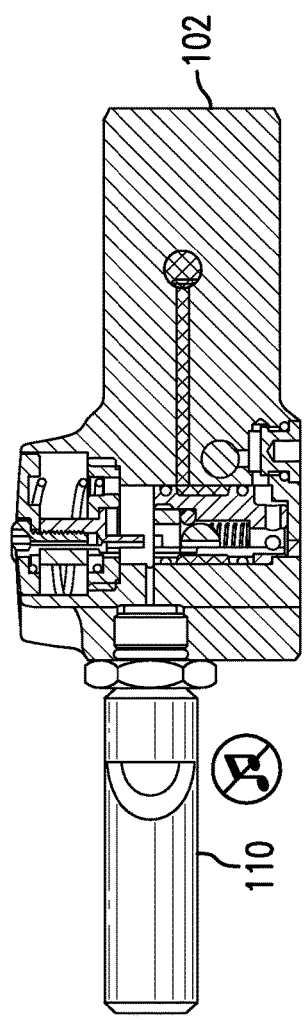
FIG.17A
FIG.17B

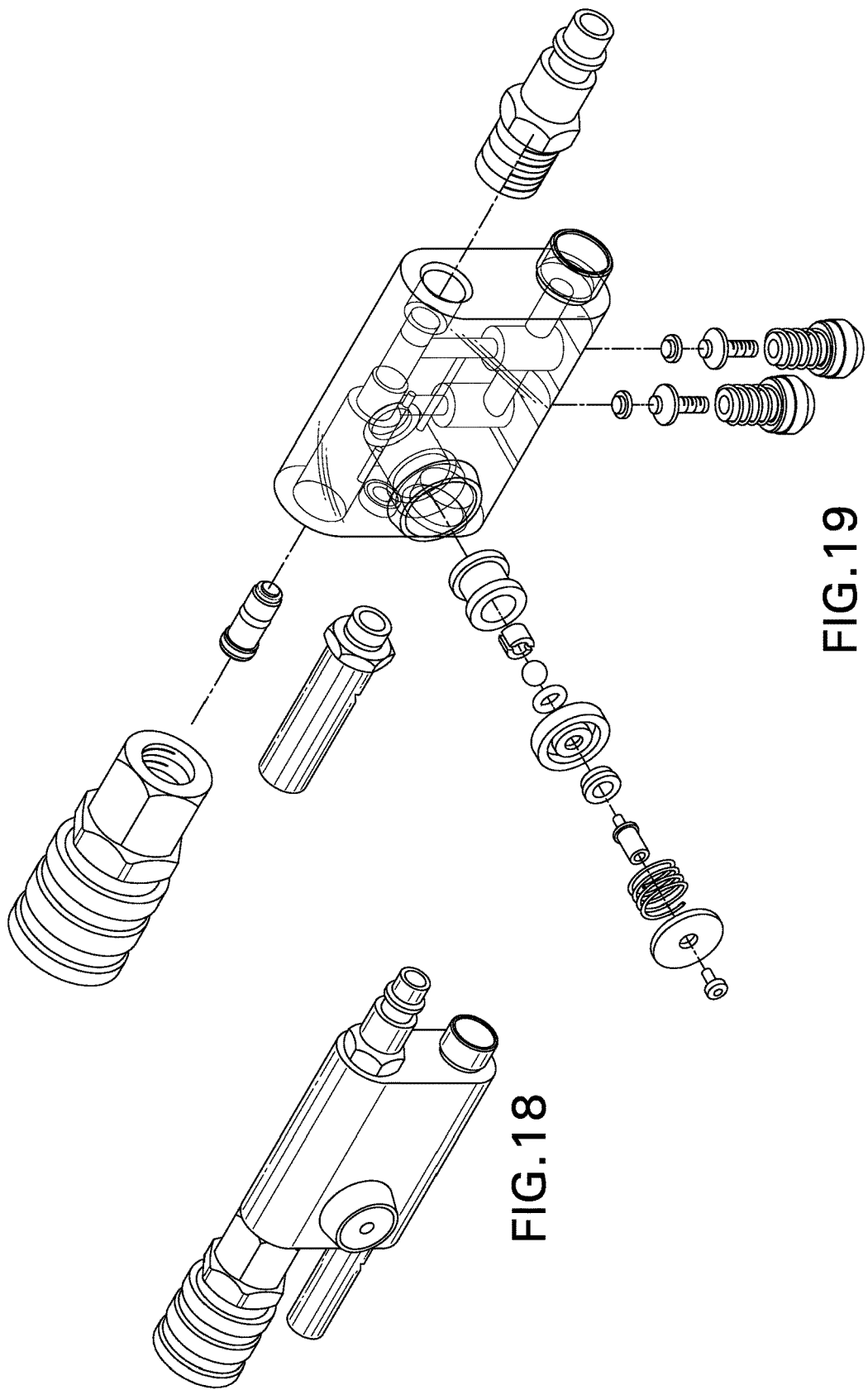

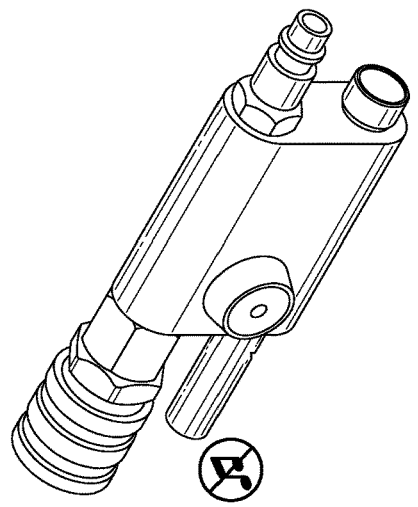
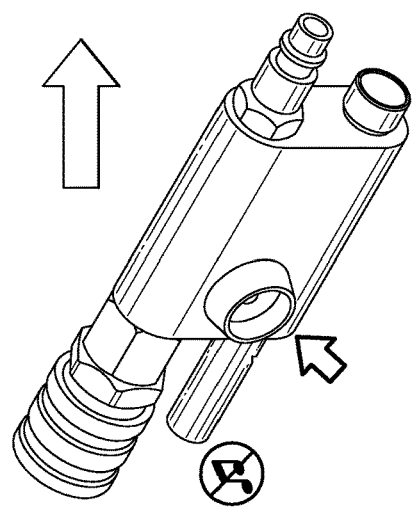
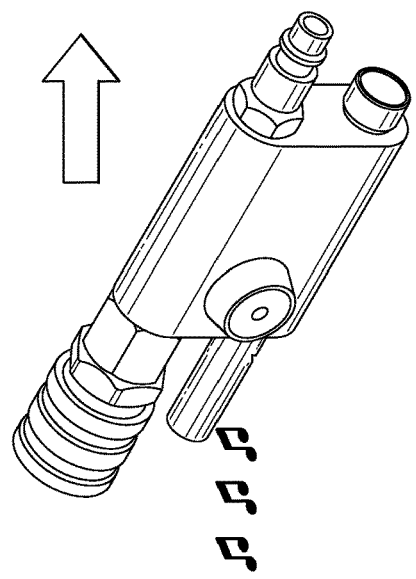
FIG.20

AUTOMATIC SWITCHING DEVICE FOR A BREATHING APPARATUS WITH AN ALARM-RELIEF FUNCTION AND AUTOMATIC RESET

CROSS-REFERENCE TO RELATED APPLICATIONS

This application claims the priority to PCT Application No. PCT/US2014/012684 (entitled AUTOMATIC SWITCHING DEVICE FOR A BREATHING APPARATUS WITH AN ALARM-RELIEF FUNCTION AND AUTOMATIC RESET, filed Jan. 23, 2014); which claims priority to U.S. Patent Provisional Application Ser. No. 61/762,729 (entitled AUTOMATIC SWITCHING DEVICE FOR A BREATHING APPARATUS WITH AN ALARM-RELIEFING FUNCTION AND AUTOMATIC RESET, filed Feb. 8, 2013) such that the present application also claims priority to U.S. Provisional Patent Application Ser. No 61/762,729, all of which are incorporated herein by reference.

TECHNICAL FIELD

Various embodiments relate generally to an automatic switching device having an alarm for providing notification of a switching procedure from a supplied air source to a backup air source and further to an operative assembly for manually disabling the alarm and for permitting an automatic reset of the alarm upon a return to the supplied air source from the backup air source.

BACKGROUND

Breathing apparatuses are widely used in settings in which people risk exposure to dangerous airborne hazards. Various types of breathing devices are employed to provide protection against various dangers. For example, some breathing filters provide protection against particle contaminants. Some breathing apparatuses provide filtration of chemical hazards. Other breathing devices provide defense against nuclear unstable gaseous elements.

In some industrial situations, workers may breathe breathable air provided to them from safe sources. Some workers wear air tight suits which may be supplied clean air via a hose or air line. Some workers may carry clean air in a cylinder or compressed-air tank. Scuba divers may carry one or more air tank on their back, each of which may provide breathable air to the divers while underwater.

SUMMARY

Apparatus and associated methods relate to an automatic fluid alarm that provides a fluid-communication path between a secondary fluid source and a whistle port when a primary fluid source experiences a reduction in pressure, the automatic fluid alarm being user resettable by disconnecting the primary fluid source or otherwise reducing the primary source pressure and activating a reset member, thereby interrupting the fluid-communication path. In some examples, a piston member may provide a movable seal for providing the fluid-communication path and its interruption. An exemplary piston member may be slidably reset in a non-interrupting mode by an adequate primary fluid pressure, and slidably set in an interrupting mode by a user activation. The interrupting mode may silence the whistle which may facilitate user communication during what may be a stressful primary fluid source failure event. Some exemplary automatic fluid alarms may conserve secondary fluid when the whistle is silenced.

Various embodiments may achieve one or more advantages. For example, some embodiments may encourage a user to disconnect a primary fluid source that has been compromised. A user then may silence the alarm so as to preserve a limited secondary fluid source. This preservation of the secondary fluid source may extend the time in which the secondary fluid source may be used by the user. In some embodiments, the silencing of the whistle may facilitate communications between the user and other workers following the primary fluid source failure. For example, the user may use a communication device to speak with workers outside of the contaminated environment without having to compete with an alarm whistle. In some embodiments, such communication fidelity may promote a successful rescue of a worker without a primary fluid source.

The details of various embodiments are set forth in the accompanying drawings and the description below. Other features and advantages will be apparent from the description and drawings, and from the claims.

BRIEF DESCRIPTION OF THE DRAWINGS

FIGS. 1-3 depict, in front and side views, an exemplary switching device.

FIG. 5 depicts a dimensional view of the exemplary switching device.

FIG. 7 depicts an exemplary piston assembly for directing airflow.

FIG. 12 depicts an exemplary end plug assembly.

FIG. 13 depicts the exemplary sleeve for being fitted around a device body.

FIGS. 14A-14B depict the exemplary switching device in a normal work mode.

FIGS. 16A-16B depict the exemplary switching device with an alarm being operatively relieved.

FIGS. 17A-17B depict the exemplary switching device after an alarm has been operatively relieved.

FIGS. 18-20 depict, in perspective views, an exemplary automatic switching device in assembled, disassembled, and operational views.

Like reference symbols in the various drawings indicate like elements.

DETAILED DESCRIPTION OF ILLUSTRATIVE EMBODIMENTS

Figure 15A:
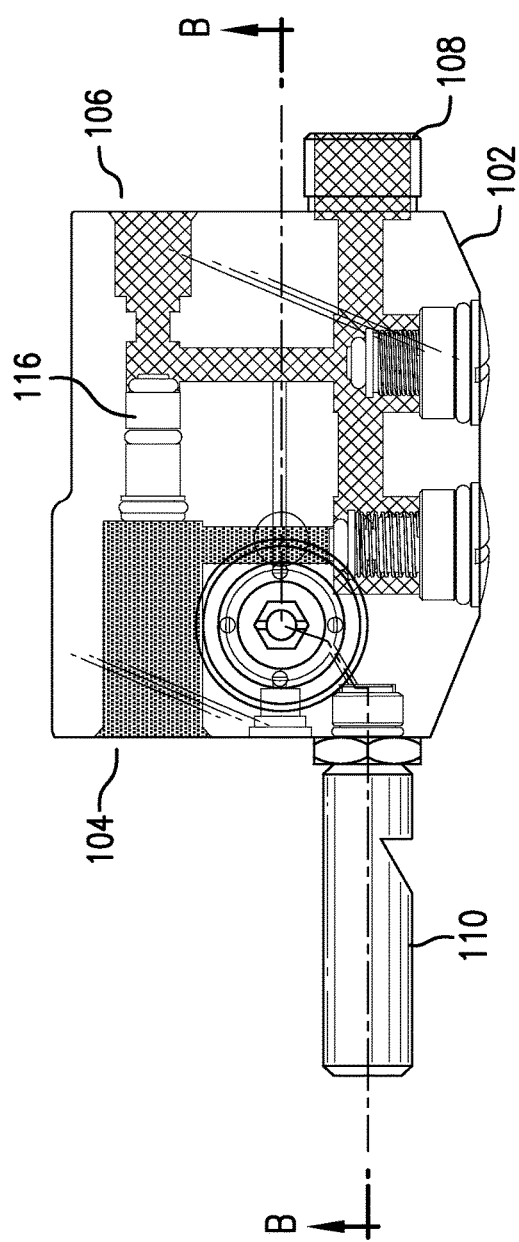
FIGS. 15A-15B depict the exemplary switching device after being provided an abnormal air supply.
Figure 15B:
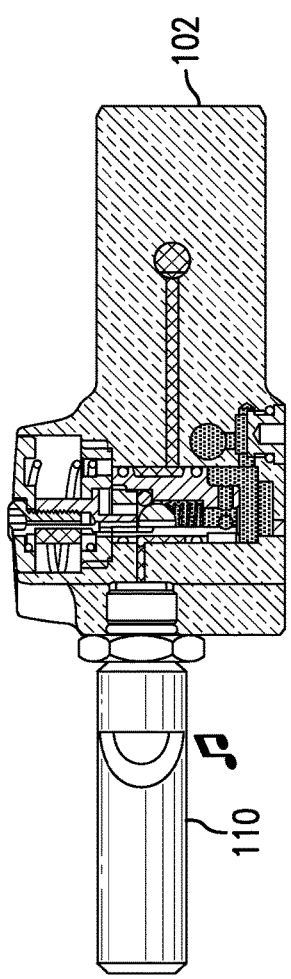

To aid understanding, this document is organized as follows. First, an exemplary switching device having an alarm-relief button and automatic reset capabilities is briefly introduced with reference to FIGS. 1-3. Then, with reference to FIGS. 4-13, the discussion turns to details of exemplary components that provide functionality to the exemplary switching device. Next, an exemplary operation cycle of the switching device is illustrated in FIGS. 14A-17B. Specifically, FIGS. 14A-14B illustrate the switching 25 device in a normal work mode in which supplied industrial air is outputted. Next, FIGS. 15A-15B illustrate a switching procedure caused by an abnormally low supply of industrial air, which has an effect of simultaneously activating an alarm and permitting backup air to flow. Then, FIGS. 16A-17B illustrate a process of deactivating the alarm in a manner that permits the alarm to automatically reset upon subsequent connection and flow of a normal supply of industrial air. Finally, with reference to FIGS. 18-23, additional representations of an exemplary switching device and operative procedures of the switching device are shown.

FIGS. 1-3 depict, in front and side views, an exemplary switching device. A front view of a switching device 100 is shown in FIG. 1. In an exemplary embodiment, the switching device 100 may be used with a breathing apparatus to provide an automatic and uninterrupted flow of a fluid. In addition, the switching device 100 may provide an audible alarm in the case of abnormal supplied industrial fluid. The audible alarm may be deactivated manually by the user and the audible alarm may be automatically reset upon reconnection of a normal supplied industrial fluid. In an exemplary embodiment, a "normal" industrial supplied fluid may be a supplied fluid flowing at a pressure suitable for an intended application, such as for example a breathing apparatus.

In an exemplary embodiment, the fluid may be breathable air to be delivered to a patient for a breathing apparatus. In other exemplary embodiments, the fluid may be a liquid or other gaseous substances rather than air. For example, a medicinal liquid may be delivered to a patient through the switching device. For simplicity, the fluid that is directed through the switching device 100 will be referred to herein as "air".

The switching device 100 includes a device body 102 for providing one or more routes for air to flow. The device body 102 has a supplied air input 104, a backup air input 106, and an air output 108. The air inputs 104, 106 and air output 108 may be mechanically structured to couple with various mechanical connectors suited for providing a leak-free connection interface to the device body 102. In some exemplary embodiments, the mechanical connections may be provided through a tool-less quick connector.

In an exemplary embodiment, the supplied air input 104 may be in fluid communication with a normally constant source of generated air or a large tank of stored air suited to deliver air for long periods of time, such as for example a supplied industrial air. In an exemplary embodiment, the backup air input 106 may be in fluid communication with a smaller tank of stored air suited to provide backup air for a limited period of time, such as for example a compressed air cylinder.

The switching device 100 also includes an alarm whistle 110 for providing notification of use of the backup air source and an alarm-relief button 112 for disabling the alarm whistle 110.

A first side angle view of the switching device 100 is shown in FIG. 2. As illustrated, the backup air input 106 may be located on the same side of the device body 102 as the air output 108. In other exemplary embodiments, the backup air input 106 may be located elsewhere upon the device body 102, such as for example the same side as the supplied air input 104.

A second side angle view of the switching device 100 is shown in FIG. 3. As illustrated, multiple end plug assemblies 114 may be located upon the device body 102. The end plug assemblies 114 will be described in greater detail with reference to FIG. 12.

Figure 4:
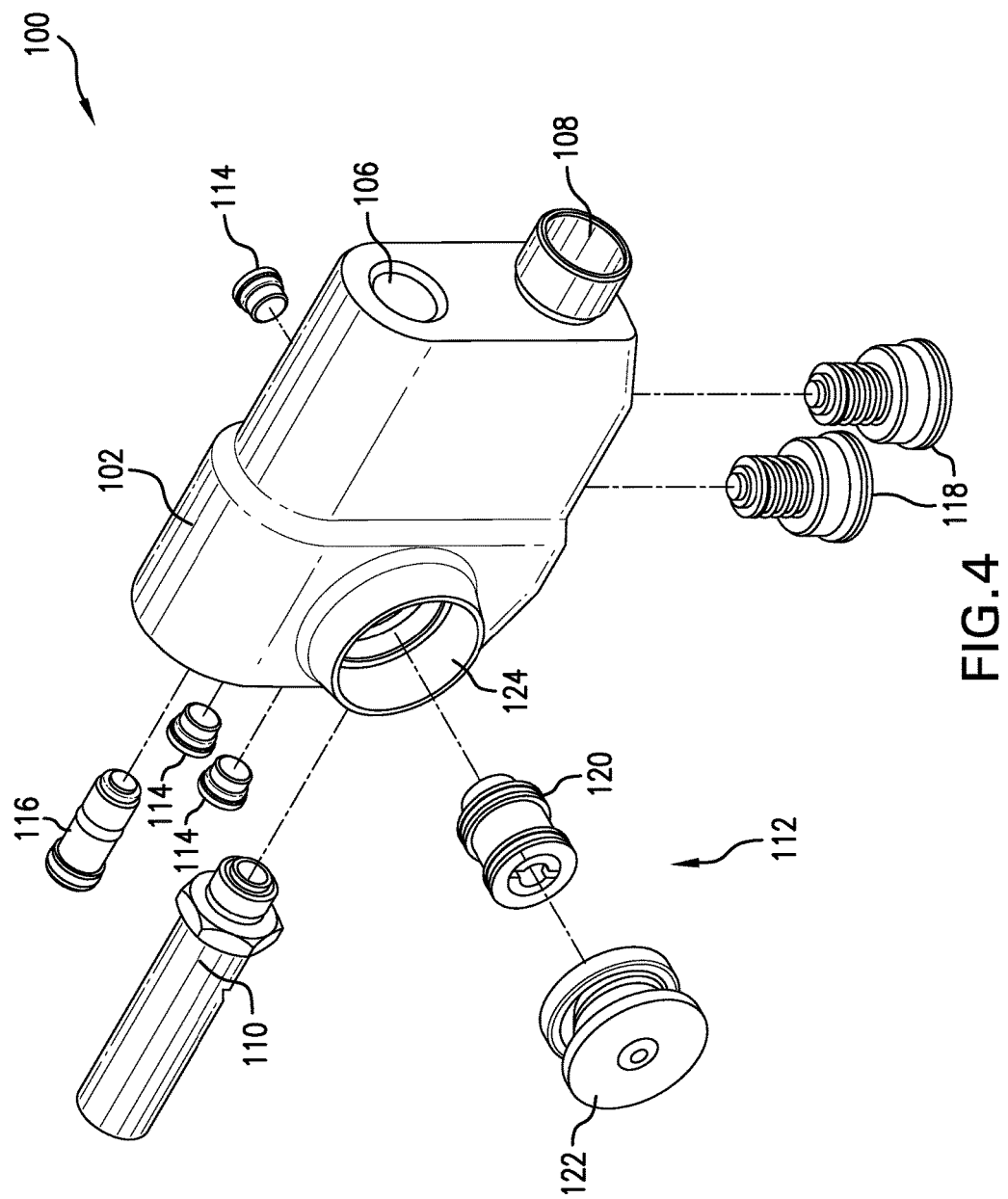
FIG. 4 depicts, in an exploded view, the exemplary switching device.

FIG. 4 depicts, in an exploded view, the exemplary switching device 100. In addition to the device body 102, supplied air input 104, backup air input 106, air output 108, alarm whistle 110, alarm-relief button 112, and end plug assemblies 114 as previously mentioned, the switching device 100 may include multiple throttle valve assemblies 118, an alarm-relief piston assembly 120, and a press button assembly 122. The piston assembly 116 and throttle valve assemblies 118 direct airflow within the device body 102 and will be described in greater detail with reference to FIGS. 7 and 8. The alarm-relief piston assembly 120 and the press button assembly 122 couple to form the press button assembly 122. The press button assembly 122 may couple to the device body 102 via an opening 124. The alarm-relief piston assembly 120 and the press button assembly 122 will be described in greater detail with reference to FIGS. 10 and 11.

FIG. 5 depicts a dimensional view of the exemplary switching device. The exemplary switching device 100 includes the device body 102 which may be of a small stature, handheld structure that is easily maneuverable. In the exemplary embodiment illustrated by FIG. 4, the device body 102 has a length of 58 millimeters, a width of 48 millimeters, and a thickness of 31 millimeters. In the exemplary embodiment, the device body 102 and alarm whistle combined have a length of 96 millimeters. As shown, the supplied air input 104, backup air input 106, and air output 108 may connect to flexible hoses.

In an exemplary embodiment, the device body 102 may be manufactured from a metal alloy. For example, the device body 102 may be manufactured from a brass, steel, or aluminum material. In some exemplary embodiments, the device body 102 may be formed from a hard plastic material, which may be formed of components produced via an injection molding process, for example. In an exemplary embodiment, the switching device 100 may have a weight of approximately 350 grams.

Figure 6B:
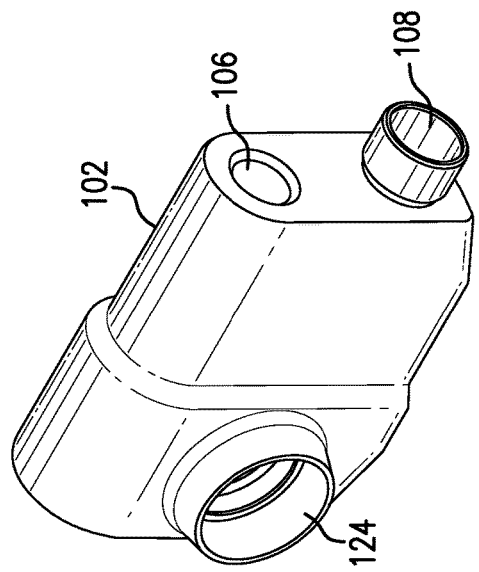
FIGS. 6A-6D depict, at various angles, an exemplary device body for the switching device.
Figure 6D:
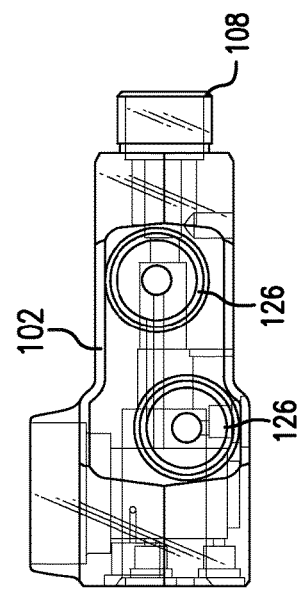
Figure 6A:
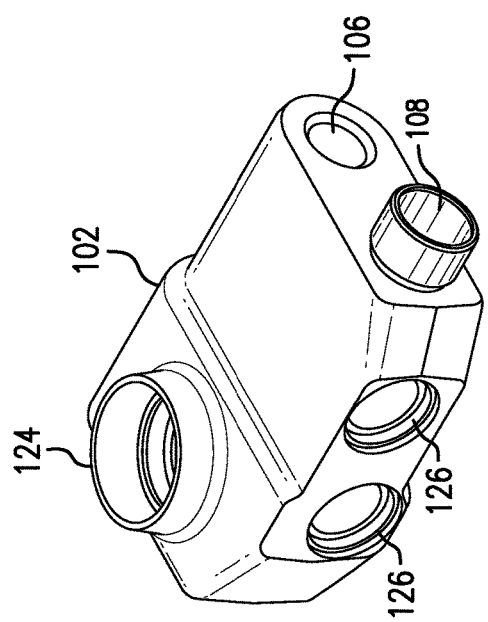
Figure 6C:
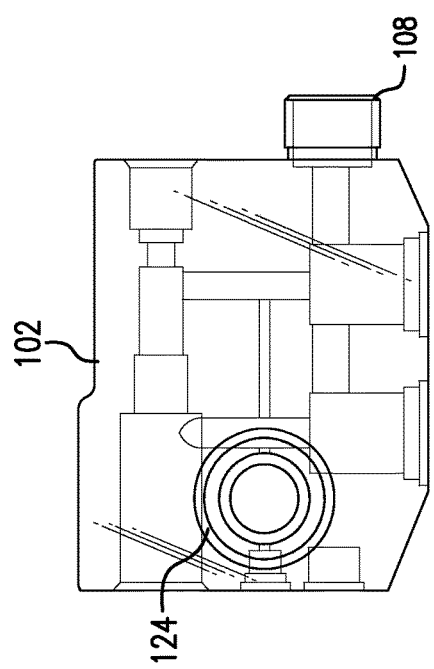

FIGS. 6A-6D depict, at various angles, an exemplary device body for the switching device. The device body 102 may be formed as a one-piece structure. The device body 102 includes multiple internal paths as shown in FIGS. 6C and 6D to permit airflow to pass from the supplied air input 104 to the air output 108 and also from the backup air input 106 to the air output 108. The device body 102 includes multiple openings, such as the opening 124 for the press button assembly 122 and openings 126 for the throttle valve assemblies 118. In some exemplary embodiments, the openings 124, 126 may be threaded to permit attachment and detachment of internal and external components.

FIG. 7 depicts an exemplary piston assembly for directing airflow. The piston assembly 116 is adapted to direct air travel within the interior of the device body 102. In an exemplary embodiment, the piston assembly 116 may be forced to a first position as shown in FIG. 14A or a second position as shown in FIG. 15A dependent upon whether air is being supplied through the supplied air input 104 or the backup air input 106. The piston assembly 116 includes a piston 128 to form a main body of the piston assembly 116 and a series of sealing members (e.g., O-rings) 130 attached around the piston 128 for forming a seal around the edges of the piston 128 to restrict air travel along a length of the piston 128. In some exemplary embodiments, the sealing members 130 may be attached at each end of the piston 128 and also between the ends of the piston 128 to provide multiple sealing points. In some embodiments, the piston 128 may be formed of a metal material.

Figure 8:
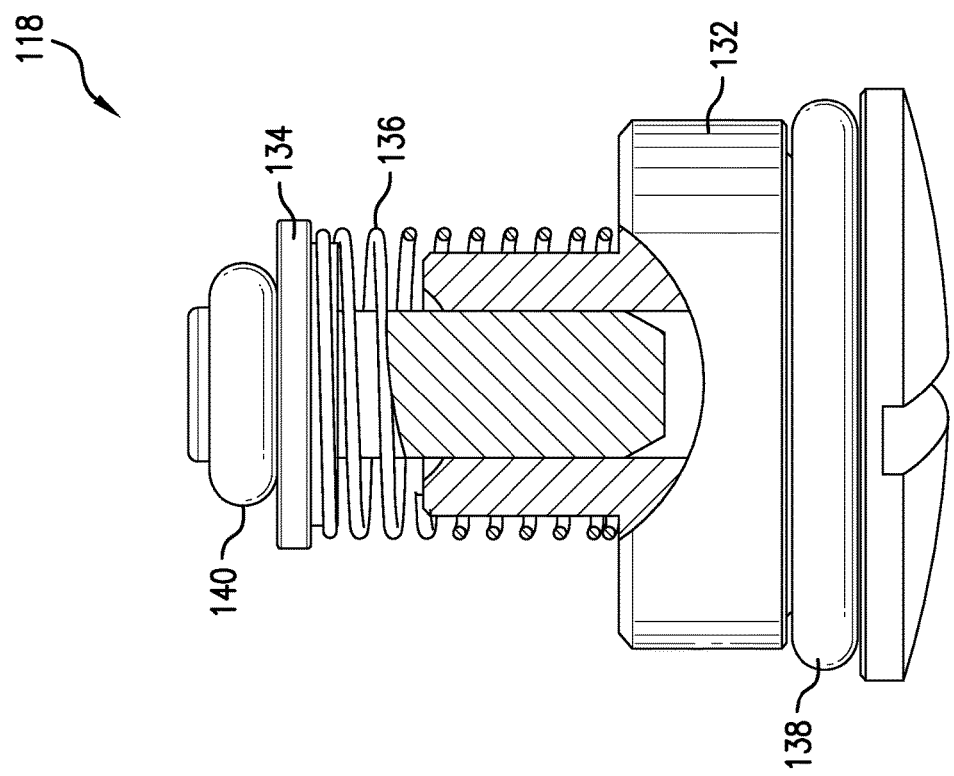
FIG. 8 depicts an exemplary throttle valve assembly for directing airflow.

FIG. 8 depicts an exemplary throttle valve assembly 118 for directing airflow. The throttle valve assembly 118 includes a valve seat 132 connectable to the device body 102 and a throttle valve 134 movably connected to the valve seat 132. The throttle valve 134 moves relative to the valve seat 132 to permit and restrict airflow through the device body 102. The throttle valve assembly 118 may also include multiple sealing members (e.g., O-rings) 138, 140 to restrict inadvertent leakage around or past the throttle valve assembly 118. In some exemplary embodiments, the throttle valve assembly 118 may be removable from the device body 102, such as for example to permit cleaning or replacement.

In an exemplary embodiment, a spring 136 may exert an outward force upon the throttle valve 134 relative to the valve seat 132. For example, a compressed air provided through the supplied air input 104 may overcome the force of the spring 136 such as to force the throttle valve 134 towards the valve seat 132 and permit air to flow through the device body 102 and to the air output 108. In an exemplary embodiment, if the pressure of the compressed air passing through the supplied air input 104 lessens to a degree less than the compression force of the spring 136, the spring 136 may force the throttle valve 134 outwards relative to the valve seat 132 to block passage of air flow from the supplied air input 104 to the air output 108. As illustrated in reference to FIGS. 14A-17B, multiple throttle valve assemblies 118 may be used to control air flow through the device body 102 from the supplied air input 104 and/or the backup air input 106. In an exemplary embodiment, the throttle valve 134 and valve seat 132 may be formed of a metal material.

Figure 9:
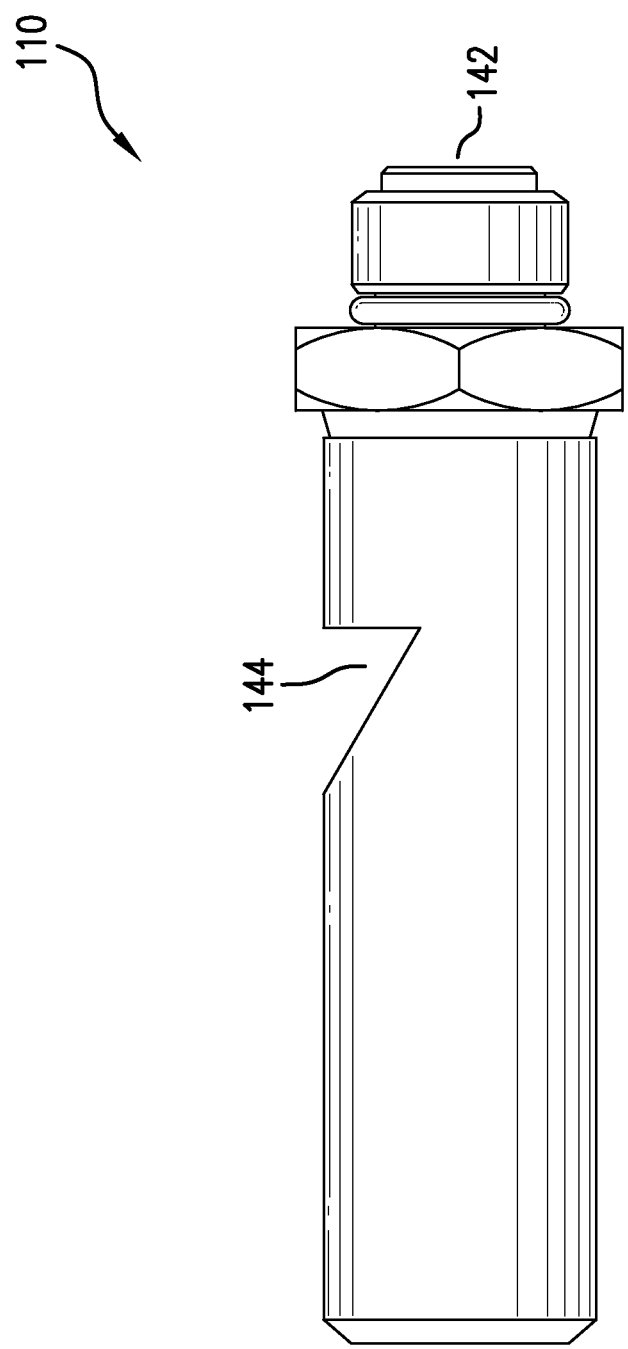
FIG. 9 depicts an exemplary alarm whistle.

FIG. 9 depicts an exemplary alarm whistle. The alarm whistle 110 outputs an audible noise to provide an alert notification that the supplied air input 104 has been interrupted and the backup air input 106 is in use. In some exemplary embodiments, the alarm whistle 110 may be removed from the device body 102, such as for example to permit cleaning or replacement.

The alarm whistle 110 includes a whistle inlet 142 for receiving a portion of the backup air passing through the device body 102. The alarm whistle 110 also includes a whistle mouth 144. The whistle mouth 144 permits the air received by the whistle inlet 142 to be released from the alarm whistle 110. In an exemplary embodiment, the alarm whistle 110 may be formed of a metal alloy. In some embodiments, the alarm whistle 110 may be powered by pneumatics. Some embodiments may provide an alarm whistle 110 that outputs a sound level of approximately 90 decibels. Some embodiments may provide an alarm whistle 110 that outputs an audible alert having a frequency between 2000 and 4000 Hertz. Some embodiments may provide an alarm whistle 110 having an air consumption of about 5 liters per minute at 0.7 megapascals pressured air.

Figure 10:
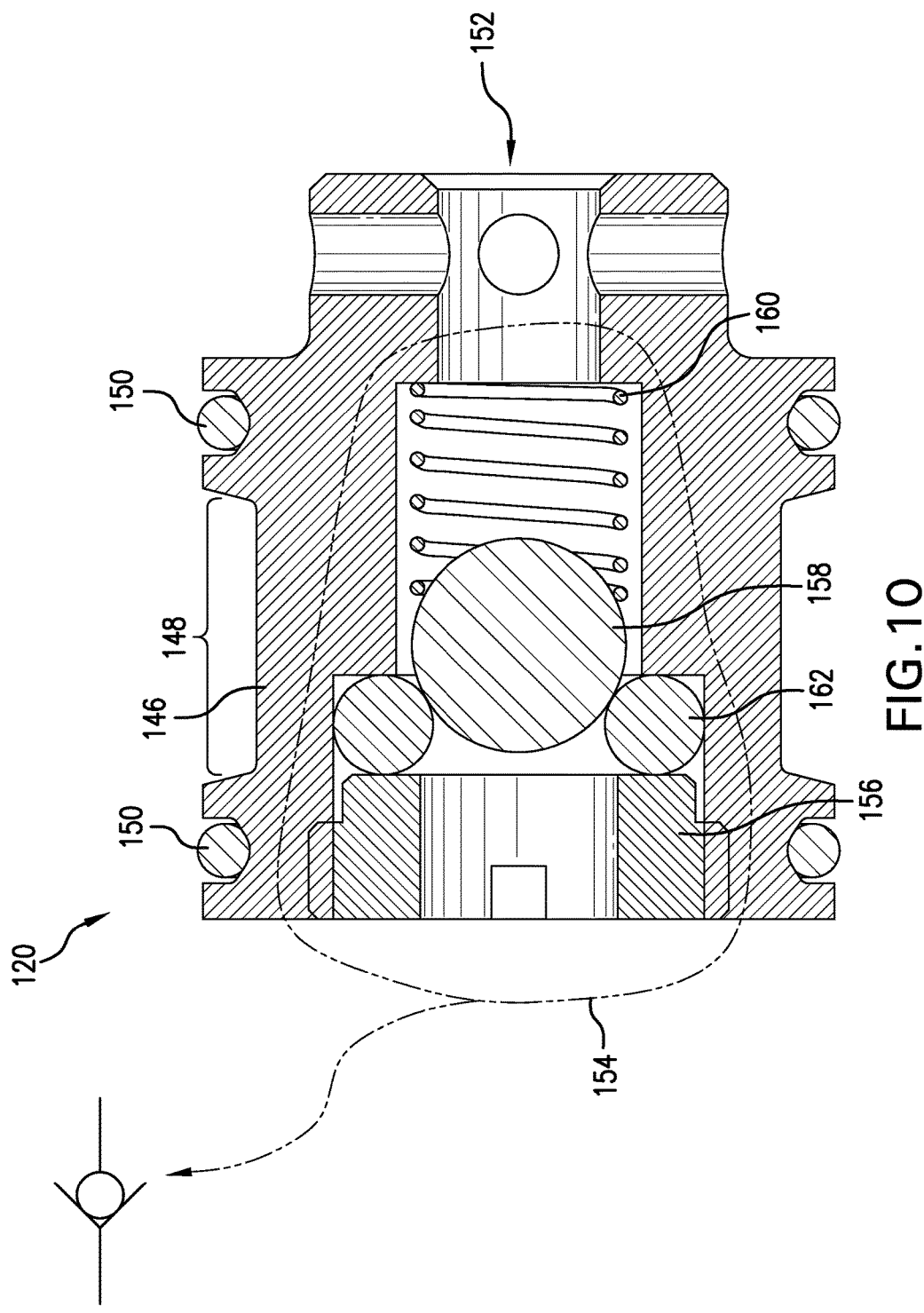
FIG. 10 depicts an exemplary alarm-relief piston assembly.

FIG. 10 depicts an exemplary alarm-relief piston assembly. The alarm-relief piston assembly 120 dictates whether air is received by the alarm whistle 110. The alarm-relief piston assembly 120 includes a piston 146 that is movable within the device body 102. The piston 146 has an exterior channel 148 that extends inwardly around an exterior peripheral edge of the piston 146 to permit air to pass around the piston 146. In some embodiments, the piston 146 may be formed from a metal alloy. The piston 146 also includes sealing members (e.g., O-rings) 150 on either side of the exterior channel 148 to restrict airflow around the piston 146 except through the exterior channel 148. The piston 146 also includes an interior channel 152 having a one-way directional valve 154 movably located within the interior channel 152.

The one-way directional valve 154 includes a locknut 156 for providing interconnection to the press button assembly 122. The one-way directional valve 154 also includes a movable ball 158, a spring 160, and a sealing member (e.g., O-ring) 162.

Figure 11:
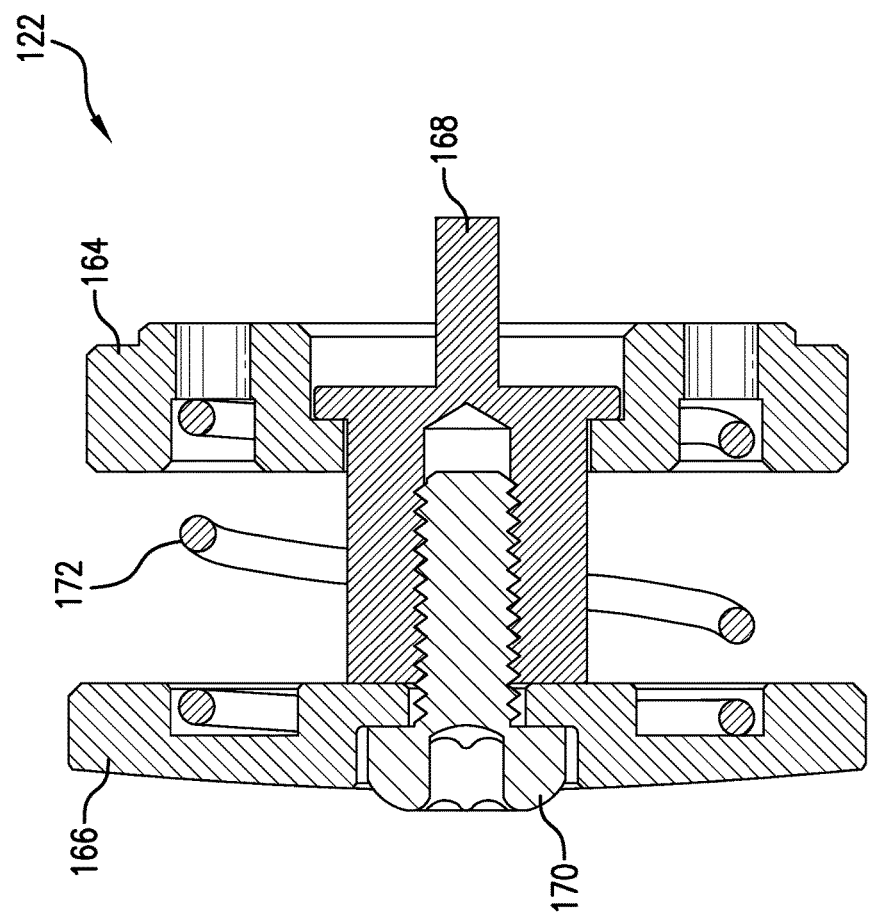
FIG. 11 depicts an exemplary press button assembly for coupling to the alarm relief piston assembly.

FIG. 11 depicts an exemplary press button assembly for coupling to the alarm relive piston assembly. The press button assembly 122 may be a user interface to operate the alarm-relief piston assembly 120. The press button assembly 122 includes a coupling nut 164 for mechanically coupling to the device body 102. The press button assembly 122 also includes a pushing plate 166 for providing user access to the press button assembly 122. The pushing plate 166 may be viewable and accessible from an exterior of the device body 102. Connecting the pushing plate 166 and the coupling nut 164 are a pushing needle 168 and a screw 170. The pushing needle 168 may be configured to apply a force upon the piston 146 and/or the ball 158 of the one-way directional valve 154 to cause a shift, blockage, or free passage of air flow. The press button assembly 122 may include a spring 172 to provide a resilient force upon the pushing plate 166 to return and automatically reset the pushing plate 166 to an initial, non depressed position.

The press button assembly 122 and the alarm-relief piston assembly 120 may be adapted to automatically reset upon a reconnection of the supplied air through the supplied air input 104 as will be illustrated in FIGS. 14A-17B. In some embodiments, the locknut 156, coupling nut 164, pushing plate 166, and pushing needle 168 may be formed from a metal material.

FIG. 12 depicts an exemplary end plug assembly. The end plug assembly 114 may sealably attach to the device body 102 to fill holes or openings in the device body 102. The end plug assembly 114 includes an end plug 174 and a sealing member (e.g., O-ring) 176. In some exemplary embodiments, the end plug 174 may threadably attach to the device body 102 such as to permit removable attachment. In some embodiments, the end plug 174 may be formed from a metal material.

FIG. 13 depicts the exemplary sleeve for being fitted around a device body. A sleeve 178 may be formed to fit around the device body 102. The sleeve 178 includes openings for access to inputs and outputs, as well as openings to permit access to the various valves and plugs of the switching device 100. The sleeve 178 may include a movable portion that coordinates with the press button assembly 122 to permit for operation of the press button assembly 122 while the sleeve 178 is fitted around the switching device 100. In some exemplary embodiments, the sleeve 178 may be formed from a rubber material.

FIGS. 14A-14B depict the exemplary switching device in a normal work mode. FIGS. 14A-14B illustrate the switching device 100 in front and sectional views during a normal work mode both. The air may be supplied to the output through a primary air source via the supplied air input 104. The interior ports of the switching device 100 are shown to illustrate the directional path of the air through the switching device 100.

For example, the primary source of air (e.g., supplied industrial air) enters the device body 102 through the supplied air input 104. The supplied industrial air supplied through the supplied air input 104 has a pressure about equal to or greater than the pressure of the backup air supplied through the backup air input 106. The equal to or greater to pressure causes the piston assembly 116 to shift towards the backup air input 106 and prevent backup air from flowing through the device body 102 to the air output 108.

The supplied industrial air travels through the interior ports of the device body 102 causing the throttle valve assemblies 118 to move towards a position that permits the supplied industrial air to reach the air output 108. For example, a first down-line throttle valve assembly 118 may be forced to a compressed position to permit travel of the supplied industrial air and a second down-line throttle valve assembly 118 may be forced to an extended position to restrict travel of backup air as shown in FIG. 14A.

The alarm-relief piston assembly 120 is also pushed up by the supplied industrial air to maintain the one-way directional valve 154 in a closed position and restrict air passage to the alarm whistle 110 as shown in FIG. 14B.

FIGS. 15A-15B depict the exemplary switching device after being provided an abnormal air supply. FIGS. 15A-15B illustrate the switching device 100 in front and sectional views after being supplied abnormal supplied air. The interior ports of the switching device 100 are shown to illustrate the directional path of the air through the switching device 100. In the depicted example, the pressure of the supplied industrial air drops below the pressure of the backup air which causes the piston assembly 116 to shift to a position towards the supplied air input 104 and thus permit travel of the backup air within the interior ports of the device body 102.

For example, the supplied air may drop from a level of about 0.7 Mpa to a level of about 0.4 Mpa to cause the backup air to take over as the delivered air source to the air output. In an exemplary embodiment, a decrease in the supplied air to around 4-5 bar may cause a switch from supplied air to backup air. In an exemplary embodiment, an increase in supplied air to a level of around 5-5.8 bar may cause a switch back to supplied air from backup air.

The backup air travels through the interior ports of the device body 102 causing the throttle valve assemblies 118 to move towards a position that permits the backup air to reach the air output 108. For example, the first down-line throttle valve assembly 118 is forced to a compressed position to permit travel of the backup air and a second down-line throttle valve assembly 118 is forced to an extended position to restrict travel of supplied industrial air as shown in FIG. 15A.

The backup air also travels through another interior port and through the exterior channel 148 of the alarm-relief piston assembly 120 and subsequently through the alarm whistle 110, thus causing the audible alarm as shown in FIG. 15B. In the depicted example, the supplied industrial air may still be flowing to the one-way directional valve 154 of the alarm-relief piston assembly 120 substantially restricting a deactivation of the audible alarm. For example, even though the pressure of the supplied industrial air may be minimal, the pressure may still be great enough to retain the alarm-relief piston assembly 120 in an upward position such as to permit flow of the backup air to the whistle. If the user were to overcome the force of the supplied industrial air upon the one-way directional valve 154 via exerting a great enough force upon the press button assembly 122, the supplied industrial air may escape through the alarm whistle 110, thus restricting deactivation of the audible alarm.

FIGS. 16A-16B depict the exemplary switching device with an alarm being operatively relieved. FIGS. 16A-16B illustrate the switching device 100 in front and sectional views after the press button assembly 122 is depressed to deactivate the audible alarm. The interior ports of the switching device 100 are shown to illustrate the directional path of the air through the switching device 100. To deactivate the audible alarm provided by the alarm whistle 110, the supplied industrial air should be disconnected from the supplied air input 104 or the pressure of the supplied industrial air should be reduced to a minimal amount.

After the supplied industrial air is disconnected or relieved from entering the device body 102, the press button assembly 122 is depressed. As the press button assembly 122 is depressed, the alarm-relief piston assembly 120 is caused to be pushed down such that the exterior channel 148 of the alarm-relief piston assembly 120 fails to align with the alarm whistle 110. Thus, the backup air being directed to the exterior channel 148 does not reach the interior port of the device body 102 leading to the alarm whistle 110 as shown in FIG. 16B.

Additionally, the pushing needle 168 of the press button assembly 122 depresses the ball 158 of the one-way directional valve 154 to permit residual supplied industrial air remaining in the interior ports to escape through the alarm whistle 110. Once all of the supplied industrial air has been depleted from the device body 102, there will be no remaining vertical forces acting upon the alarm-relief piston assembly 120. The backup air may continue to flow through the exterior channel 148 of the alarm-relief piston assembly 120; however the radial forces of the backup air around the alarm-relief piston assembly 120 do not cause the alarm-relief piston assembly 120 to shift positions within the device body 102.

By disabling the audible alert, remaining backup air may be conserved for use in the breathing apparatus. An initial audible alert may be the only notification required for the user or staff to gain knowledge of a problem in the supplied air and thus a continuing alert during reinstatement of the supplied air may not be necessary. By disabling the audible alert, patients and staff may be better able to communicate necessary remedies and solutions to return the supplied air source to normal functionality. In some exemplary embodiments, by disabling the audible alert, breathing air from the backup air source may be saved by about 5 liters per minute.

FIGS. 17A-17B depict the exemplary switching device after an alarm has been operatively relieved. FIGS. 17A-17B illustrate the switching device 100 in front and sectional views after the press button assembly 122 has been released. The interior ports of the switching device 100 are shown to illustrate the directional path of the air through the switching device 100.

After releasing downward pressure upon the pushing plate of the press button assembly 122, the biasing force of the spring 172 of the press button assembly 122 causes the pushing plate 166 to automatically reset to an initial, outward position. The alarm-relief piston assembly 120 will stay in the depressed position to continue to restrict air flow to the alarm whistle 110.

Once the supplied industrial air is reconnected to the supplied air input 104 at a pressure about equal to or greater than the backup air, the supplied industrial air pushes on the piston assembly 116 causing the piston assembly 116 to shift towards the backup air input 106 and thus closing the port leading to the air output 108 from the backup air input 106 to restrict travel of the backup air as shown in FIGS. 14A-14B. The supplied industrial air also pushes up on the alarm-relief piston assembly 120 to reset the alarm-relief piston assembly 120 so that the exterior channel 148 fluidly aligns with the alarm whistle 110. Thus, by reconnecting the supplied industrial air, the alarm-relief piston assembly 120 is automatically reset such that if the supplied industrial air were to become abnormal again, flowage of the backup air would again cause the alarm whistle 110 to output an audible alarm.

FIGS. 18-20 depict, in perspective views, the automatic switching device in assembled, disassembled, and operational views. Particularly, FIG. 18 depicts, in a perspective view, the exemplary switching device 100. FIG. 19 depicts, in a detailed exploded view, the exemplary switching device 100. FIG. 20 depicts an operative procedure for the exemplary switching device 100.

Figure 22:
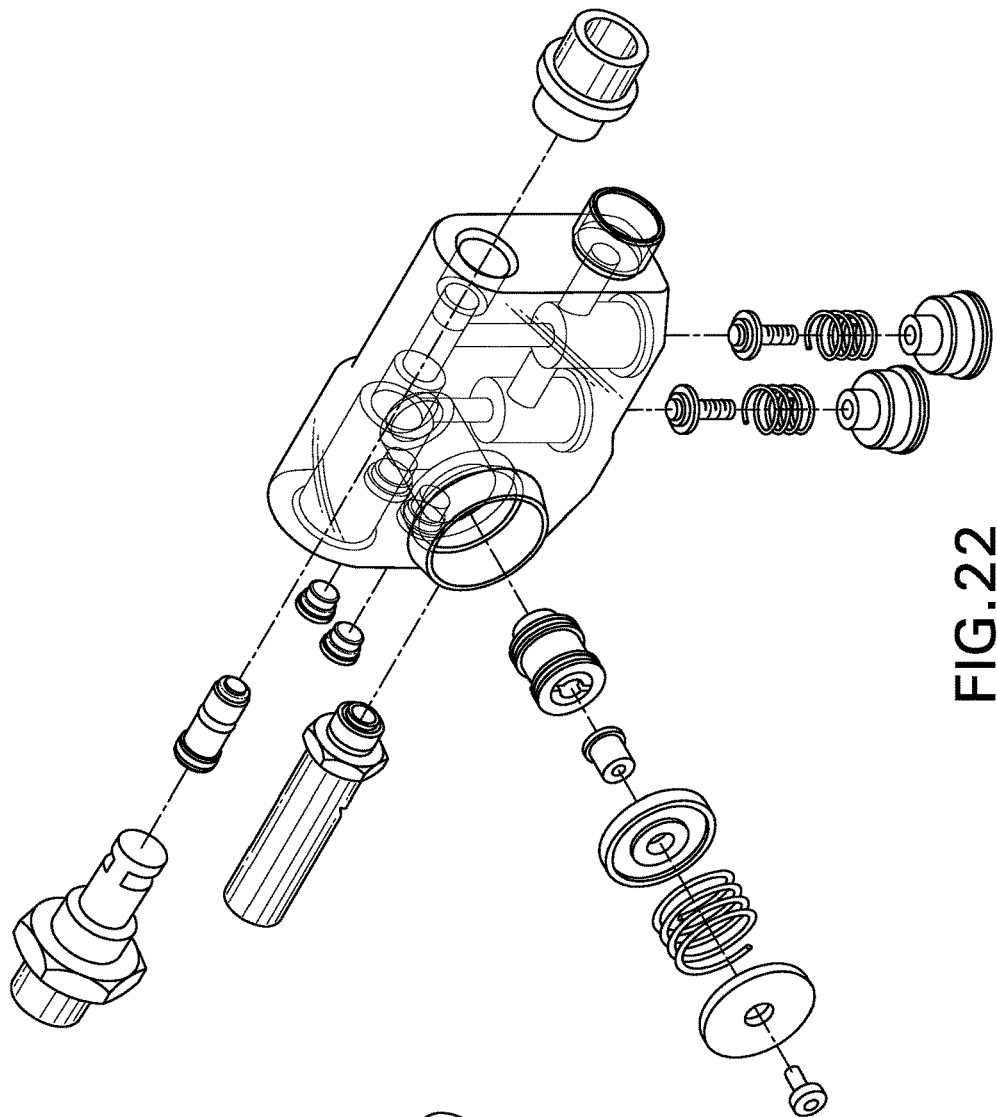
FIGS. 21-23 depict, in perspective views, another exemplary automatic switching device in assembled, disassembled, and operational views.
Figure 21:
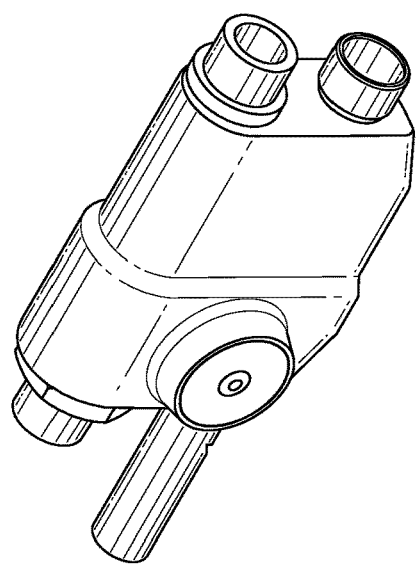
Figure 23:
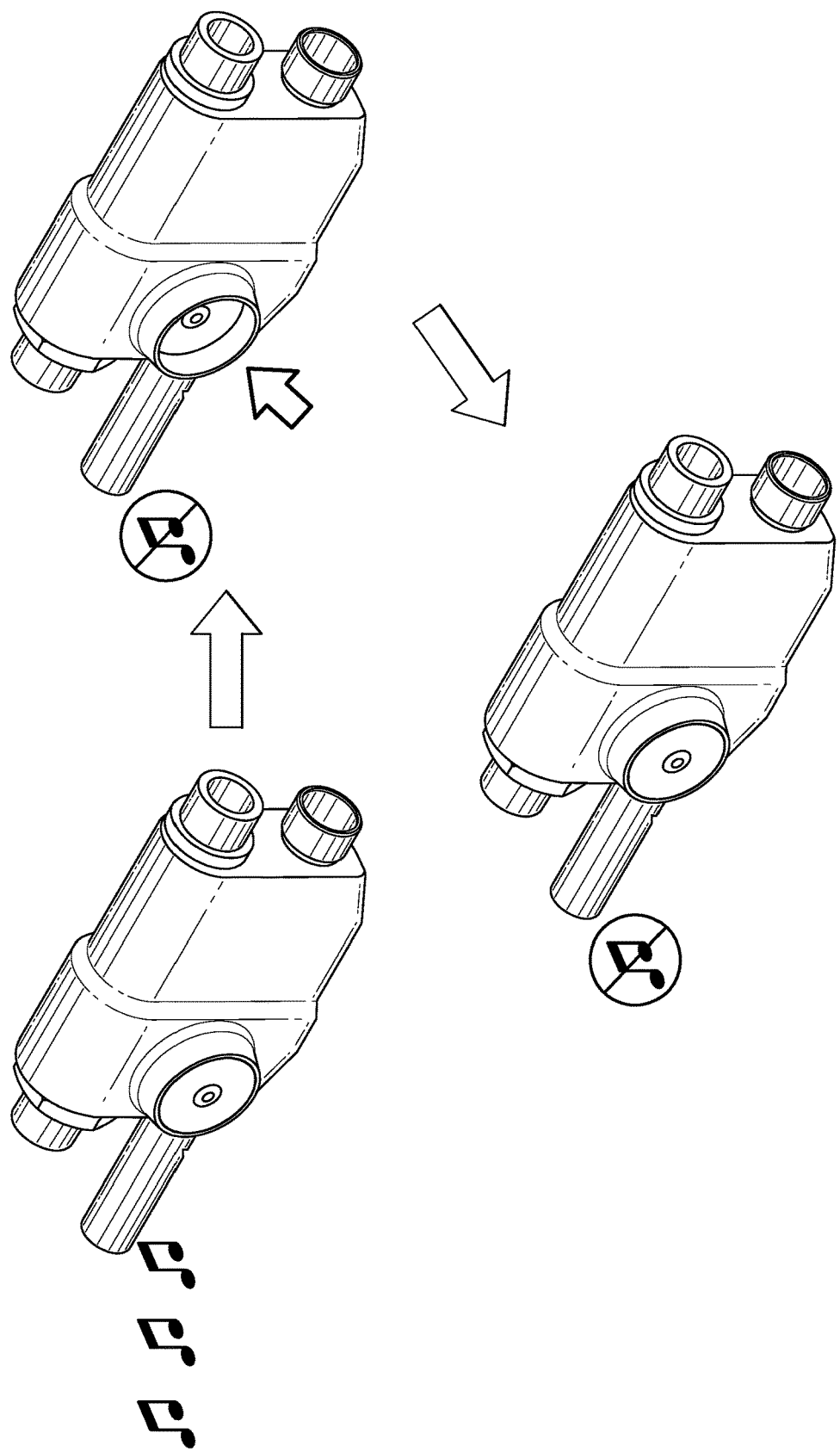

FIGS. 21-23 depict, in perspective views, another exemplary automatic switching device in assembled, disassembled, and operational views. Particularly, FIG. 21 depicts, in a perspective view, the exemplary switching device 100. FIG. 22 depicts, in a detailed exploded view, the exemplary switching device 100. FIG. 23 depicts an operative procedure for the exemplary switching device 100.

Although various embodiments have been described with reference to the Figures, other embodiments are possible. For example, in an exemplary embodiment, the switching device may include a pressure regulator to regulate a compressed air supply being delivered from the supplied air input and/or the backup air input. In some examples, the regulator may operate to maintain a relatively consistent delivered air pressure to and throughout the switching device to minimize switching from the supplied air input to the backup air input.

In an exemplary embodiment, the switching device may include one or more gauges for monitoring air flow through the switching device. For example, a first gauge may display a current pressure of the supplied air connected to the switching device. A second gauge may display a current pressure of the backup air connected to the switching device. A third gauge may display a current position of the alarm-relief piston assembly. Another gauge may display a quality of air that is being delivered to the air output through the switching device.

In various embodiments, the switching device may be embedded within or in communication with an air face mask. The small size and reduced weight of the switching device may permit for the direct attachment to an air face mask without noticeable disturbance to the wearer of the mask. In an exemplary embodiment, the switching device may be affixed to a carrying harness of a breathing apparatus.

In accordance with another embodiment, the alarm-relief button may be automatically reset from an engaged position to a disengaged position by a reconnection of a normal supplied air to the supplied air input. For example, once the normal supplied air becomes abnormal, such as for example during the loss of pressure or by becoming intermittent, the backup air supply may become the primary air source to deliver the air to the air output. At this time, the backup air may also deliver air to the alarm whistle to cause an audible alert to be engaged via the air flowing through the alarm whistle. By depressing the alarm-relief button, the passage of the backup air to the alarm whistle may be interrupted thus disabling the audible alert. By disconnecting the supplied air source or completely shutting the supplied air source off, the alarm-relief button may be able to remain in an alarm disengage position. During this time, the backup air may continue to be supplied to the air output. By reconnecting a normal supplied air through the supplied air input, the alarm-relief button may be automatically reset to a standby position (e.g., ready to disengage the alarm whistle) and the passage of the backup air to the alarm whistle may be blocked until the backup air source is again engaged due to abnormal supply air pressure. In some exemplary embodiments, the switch from supplied air to backup air may occur substantially instantaneously.

In accordance with another embodiment, the alarm whistle may be removed from the device body for cleaning, adjustment, or interchanging. For example, if an alternate tone or volume is preferred to be outputted by the alarm whistle, a secondary alarm whistle having a different structural shape may be attached to the device body in place of a primary alarm whistle. In an exemplary embodiment, a patient illness may warrant more prompt attention which may necessitate the use of an alarm whistle capable of outputting a higher decibel level.

In an illustrative embodiment, an exemplary automatic switching device may provide breathable air from a secondary air source should a primary air source fail. The automatic switching device may include a manifold module having a first main fluid-communication path from a first input port to an output port and a second main fluid-communication path from a second input port to the output port. In some embodiments, the manifold module may include an alarm cavity defined by a cavity wall extending between an enclosed end and an open end. An exemplary manifold module may include a whistle port to couple to a whistle module. Some exemplary manifold modules may include a first alarm fluid-communication path from the second main fluid-communication path to the cavity via an inlet aperture in the cavity wall. A second alarm fluid-communication path from the cavity to the whistle port via an outlet aperture in the cavity wall may be included in various embodiments. Some embodiments may include a reset fluid-communication path from the first main fluid-communication path to the cavity via an automatic reset aperture in the cavity wall.

In an illustrative embodiment, an exemplary automatic switching device may include a piston module slidably disposed in the cavity. In some embodiments, the piston module may include a user interface for slidably displacing the piston into the cavity in response to a user input. Some exemplary piston modules may include a shaft extending from the user interface into the cavity. A first seal member may be disposed around a periphery of the shaft to form a slidable seal between the shaft and the cavity wall at a first position along a length of the shaft. A second seal member may be disposed around a periphery of the shaft to form a slidable seal between the shaft and the cavity wall at a second position along the length of the shaft.

In some embodiments, the piston module may operatively slide to a first position in which the first and second alarm fluid-communication paths are in fluid communication with each other in response to: i) the first main fluid-communication path being under-pressure; ii) the second main fluid-communication path at pressure; and iii) the user having not depressed the user interface. In some embodiments, the piston module may operatively slide to a second position in which the first and second alarm fluid-communication paths are not in fluid communication with each other in response to: i) the first main fluid-communication path not being under-pressure; and ii) the user not having depressed the user interface. In an illustrative embodiment, the piston may be reset from the second position to the first position in response to the first pressure at the first main fluid-communication path rising above a predetermined threshold.

In an illustrative embodiment, an exemplary resettable fluid alarm valve may include a housing having a cylindrical piston cavity in fluid communication with: i) an alarm conduit via an alarm aperture in a cavity wall of the cylindrical piston cavity; ii) a whistle conduit via a whistle aperture in the cavity wall; and iii) a reset conduit via a reset aperture. Some embodiments may include a cylindrical piston having a user-interface surface on one longitudinal end and a fluid-actuated reset surface on an opposite longitudinal end. The cylindrical piston may longitudinally slide within the cylindrical piston cavity in a bidirectional manner between a transmit position and an interrupt position. The cylindrical piston may have a first fluid seal coupled to and circumscribing the piston and slidably coupled to the cavity wall. An exemplary resettable fluid alarm valve may include a transmission region on one side of the first fluid seal.

In an illustrative embodiment, the cylindrical piston may move to the transmit position in response to a fluid pressure in the reset conduit that exceeds a predetermined threshold. In some embodiments, the cylindrical piston may move to the interrupt position in response to the user applying a force to the user-interface surface. In an exemplary embodiment, when the cylindrical piston is in the transmit position, the alarm aperture and the whistle aperture may both be on the same side of the first fluid seal providing fluid communication between the alarm conduit and the whistle conduit via the transmission region. In an exemplary embodiment, when the cylindrical piston is in an interrupt position, the alarm aperture and the whistle aperture may be on opposite sides of the first fluid seal, the first fluid seal thereby interrupting the fluid communication between the alarm conduit and the whistle conduit.

In an illustrative embodiment, an exemplary automatic fluid switching device may include a means for providing fluid communication between a secondary fluid-communication path and a whistle port when a primary fluid pressure at the primary input port is reduced to below a predetermined threshold. For example, means for providing fluid communication between the secondary fluid-communication path and a whistle port may include an alarm valve system. Examples of which are described, for example, with reference to FIGS. 14A-17B. In some embodiments, the alarm valve system may provide fluid communication when a primary fluid pressure at a primary input port exceeds a predetermined threshold. Some exemplary automatic fluid switching devices may include means for interrupting the fluid communication between the secondary fluid-communication path and the whistle port by a user. Examples of means for interrupting the fluid communication between the secondary fluid-communication path and the whistle port are described, for example, with reference to at least FIGS. 14A-17B. For example, the alarm valve may be opened to disconnect the fluid communication in response to a user depressing a user-interface coupled to the alarm valve.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated.

What is claimed is:

1. An automatic switching device for a breathing apparatus comprising:
a body with a plurality of fluid communication paths;
a supplied air input in fluid communication with one of the plurality of fluid communication paths;
a backup air input in fluid communication with another one of the plurality of fluid communication paths;
an air output in fluid communication with yet another one of the fluid communication paths;
a pneumatic alarm whistle;
an alarm-relief valve comprising two positions, wherein when in the first position the alarm-relief valve is configured to allow fluid communication to the whistle, and when in the second position the alarm-relief valve is configured to interrupt fluid communication to the whistle;
a piston located within one of the fluid communication paths comprising two positions and configured to shift between the two positions based on a pressure difference between the supplied air input and the backup air input, wherein:
in the first position the piston prevents fluid communication from the backup air input to the alarm-relief valve and to the air output, and
in the second position, the piston allows fluid communication from the backup air input to the alarm-relief valve and to the air output; and
two throttle valves, each operable to open or close fluid communication through one of the plurality of fluid communication paths, wherein:
the first throttle valve is configured so that when open, the first throttle valve allows fluid communication to the air output from the supplied air input, and when closed, the first throttle valve prevents fluid communication to the air output from the supplied air input and prevents fluid communication towards the supplied air input from the backup air input; and
the second throttle valve is configured so that when open, the second throttle valve allows fluid communication from the backup air input to the air output, and when closed, the second throttle valve prevents fluid communication from the supplied air input to the whistle though the alarm-relief valve.

2. The device of claim 1, wherein the piston is in the first position when pressure in the supplied air input is equal to or greater than pressure in the backup air input.

3. The device of claim 2, wherein the piston moves from the first position to the second position when pressure in the supplied air input is 4-5 bar below pressure in the backup air input.

4. The device of claim 1, wherein the alarm-relief valve comprises a one-way directional valve which is in fluid communication with the supplied air input, such that the alarm-relief valve is pushed to the first position by air flow from the supplied air input.

5. The device of claim 1, wherein each of the throttle valves moves from the closed positon to the open position due to sufficient pressure in the corresponding fluid communication path.

6. The device of claim 4, wherein the alarm-relief valve further comprises a button for manually moving the alarm-relief valve from the first position to the second position, and wherein any pressure in the one-way directional valve of the alarm-relief valve substantially restricts movement of the alarm-relief valve to the second position.

7. The device of claim 6, wherein the alarm whistle, when activated by fluid communication with the backup air input, is operable to be deactivated manually, after disconnection of the supplied air input from a primary air source, by depression of the button, thereby driving the alarm-relief valve from the first to the second position.

8. The device of claim 1, wherein the alarm-relief valve is operable to reset automatically from the second position to the first position upon air flow pressure through the supplied air input being equal to or greater than the backup air input.

9. The device of claim 1, wherein upon reconnection of the supplied air input to a primary air source having pressure greater than the backup air input pressure, the alarm relief valve is operable to automatically reset from the second position to the first position.

10. The device of claim 6, wherein the alarm-relief valve further comprises an alarm-relief piston, having an exterior channel about an exterior of the alarm-relief piston to permit air passage around the alarm-relief piston, and having sealing members on each side of the exterior channel to restrict airflow around the alarm-relief piston except through the exterior channel, and wherein when a user depresses the button while supplied air pressure is in the one-way directional valve of the alarm-relief valve, such supplied air is directed to the whistle.

11. The device of claim 10, wherein the plurality of fluid communication paths comprise:
 a first main fluid communication path from the supplied air input to the air output;
 a second main fluid communication path from the backup air input to the air output; and
 an alarm fluid communication path from the second main fluid communication path to the alarm relief valve; and wherein:
 the first throttle valve is located within the first main fluid communication path;
 the second throttle valve is located within the second main fluid communication path.

12. The device of claim 11, wherein when the ala -relief valve is in the first position, the exterior channel of the alarm-relief valve is in fluid communication with both the alarm fluid communication path and the whistle.

13. The device of claim 12, wherein when the alarm-relief valve is in the second position, the exterior channel of the alarm-relief valve is not in fluid communication with the whistle; wherein the alarm-relief valve is operable to reset automatically from the second position to the first position upon air flow pressure through the supplied air input being equal to or greater than the backup air input; and wherein after reset, the exterior channel of the alarm-relief valve is in fluid communication with the whistle.

14. The device of claim 1, wherein the piston comprises a plurality of sealing members configured to form a seal between the piston and the corresponding fluid communication path to restrict air flow along a length of the piston.

15. The device of claim 5, wherein each of the throttle valves comprises:
 a sealing member operable to prevent leakage around the throttle valve, and
 a spring configured to bias the throttle valve outward toward the closed position.

16. An automatic switching device for providing breathable air from a secondary air source should a primary air source fail, the automatic switching device comprising:
 a manifold module comprising:
  a first main fluid-communication path from a first input port to an output port;
  a second main fluid-communication path from a second input port to the output port;
  a cavity defined by a cavity wall extending between an enclosed end and an open end;
  a whistle port to couple to a whistle module;
  a first alarm fluid-communication path from the second main fluid-communication path to the cavity via an inlet aperture in the cavity wall;
  a second alarm fluid-communication path from the cavity to the whistle port via an outlet aperture in the cavity wall;
  a reset fluid-communication path from the first main fluid-communication path to the cavity via an automatic reset aperture in the cavity wall;
 a control valve configured to selectively interrupt the second main fluid-communication path such that, when open, the control valve allows fluid communication from the second input port to the output port, and when dosed, the control valve prevents fluid communication from the second input port to the output port and prevents fluid communication from the first input port to the first alarm fluid-communication path; and
 an alarm-relief piston module slidably disposed in the cavity, the alarm-relief piston module comprising:
  a user interface for slid ably displacing the alarm-relief piston module into the cavity in response to a user input;
  a shaft extending from the user interface into the cavity;
  a first seal member disposed around a periphery of the shaft to form a slidable seal between the shaft and the cavity wall at a first position along a length of the shaft;
  a second seal member disposed around a periphery of the shaft to form a slidable seal between the shaft and the cavity wall at a second position along the length of the shaft,
 wherein the alarm-relief piston module is operative to slide to a first position in which the first and second alarm fluid-communication paths are in fluid communication with each other in response to:
  i) the first main fluid--communication path being under-pressure; and
  ii the user interface not being depressed by the user,
 wherein the alarm-relief piston module is operative to slide to a second position in which the first and second alarm fluid-communication paths are not in fluid communication with each other in response to:
  i) the first main fluid-communication path not being under-pressure; and
  ii) the user interface being depressed by the user,
 wherein the alarm-relief piston module is reset from the second position to the first position in response to the first pressure at the first main fluid-communication path rising above a predetermined threshold.

17. The automatic switching device of claim 16, further comprising the whistle module coupled to the whistle port.

18. The automatic switching device of claim 16, further comprising a spring-loaded user engagement member coupled to the user interface.

19. The automatic switching device of claim 16, further comprising another control valve to selectively interrupt the first main fluid-communication path in response to a first fluid pressure at the first input port being below a first predetermined threshold; wherein when the control valve for the first main fluid-communication path interrupts the first main fluid-communication path, the control valve prevents fluid communication to the reset fluid-communication path from the second input port.

20. The device of claim 16, further comprising an airflow directing piston assembly in fluid communication with the first and second main fluid communication paths and having two positions and being configured to shift between the two positions based on a pressure difference between the first and second input ports, wherein:
- in the first position, the airflow directing piston assembly prevents fluid
- communication from the second input port to the first alarm fluid-communication path and to the output port, and
- in the second position, the airflow directing piston assembly allows fluid communication from the second input port to the first alarm fluid-communication path and to the output port.

* * * * *

UNITED STATES PATENT AND TRADEMARK OFFICE
CERTIFICATE OF CORRECTION

PATENT NO. : 10,086,219 B2
APPLICATION NO. : 14/766688
DATED : October 2, 2018
INVENTOR(S) : Jimmy Zheng and Gilles Cordier Page 1 of 1

It is certified that error appears in the above-identified patent and that said Letters Patent is hereby corrected as shown below:

In the Claims

Column 12/Line 41: "though" should be "through"

Column 13/Line 10: "alarm relief" should be "alarm-relief"

Column 13/Line 37: "ala -relief" should be "alarm-relief"

Column 14/Line 17: "dosed" should be "closed"

Column 14/Line 23: "slid ably" should be "slidably"

Column 14/Line 39: "fluid--communication" should be "fluid-communication"

Column 14/Line 41: "ii" should be "ii)"

Signed and Sealed this
Ninth Day of April, 2019

Andrei Iancu
*Director of the United States Patent and Trademark Office*